United States Patent [19]
Kubota et al.

[11] Patent Number: 5,916,788
[45] Date of Patent: *Jun. 29, 1999

[54] GENETIC RECOMBINATION LASER APPARATUS AND GENETIC RECOMBINATION METHOD USING THE APPARATUS

[75] Inventors: Shigeo Kubota, Kanagawa; Werner Wiechmann; Ling Yi Liu, both of Tokyo, all of Japan

[73] Assignee: Sony Corporation, Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/728,917

[22] Filed: Oct. 11, 1996

[30] Foreign Application Priority Data

Oct. 12, 1995 [JP] Japan ................................ 7-264435

[51] Int. Cl.$^6$ .......................... C12N 13/00; C12N 5/04; H01S 3/30; H01S 3/10
[52] U.S. Cl. ........................ 435/173.4; 435/419; 372/5; 372/22; 372/23; 372/25; 372/38
[58] Field of Search ................ 435/172.1, 419, 435/173.4; 536/23.1; 372/5, 23, 25, 43, 38, 75, 22

[56] References Cited

U.S. PATENT DOCUMENTS

| | | | |
|---|---|---|---|
| 5,114,630 | 5/1992 | Lin | 264/3.1 |
| 5,272,072 | 12/1993 | Kaneko et al. | 800/276 |
| 5,570,384 | 10/1996 | Nishida et al. | 372/19 |

OTHER PUBLICATIONS

Weber et al.. Genetic micromanipulation of plant cells and organelles with a laser microbeam. Plant Cell, Tissue and Organ Culture. vol. 12:219–222, Mar. 11, 1988.

Weigand et al. Laser–induced fusion of mammalian cells adn plant protoplasts. J. Cell Science. vol. 88:145–149, Jan. 1987.

Primary Examiner—Nancy Degen
Assistant Examiner—William Sandals
Attorney, Agent, or Firm—Hill & Simpson

[57] ABSTRACT

A genetic recombination laser apparatus includes an optical system having a semiconductor laser medium for generating a semiconductor laser light, an Nd:YAG crystal, an LBO and β-BBOs for reducing the wavelength of the laser light, an acoustic optical device and a lens for converging the laser light with a reduced wavelength;. A stage for positioning the focus of the laser light converged by the lens at any arbitrary location on a specimen is provided. The energy of the laser light converged on the specimen is set at a value greater than the bonding energy of the substance composing the wall of the somatic cell. Preferably, the semiconductor laser light is converted into the fifth harmonic of an Nd:YAG laser light having a wavelength of 213 nm and a second harmonic with a wavelength of 532 nm generated in the conversion process is used as for positioning the focus of the laser light converged by the lens on the specimen. The laser apparatus is capable of boring a hole through the wall of a somatic cell of the higher plant for injecting foreign genetic material into the interior of the somatic cell to undergo genetic transformation.

3 Claims, 2 Drawing Sheets

GENETIC RECOMBINATION LASER APPARATUS AND GENETIC RECOMBINATION METHOD USING THE APPARATUS

BACKGROUND OF THE INVENTION

In general, the present invention relates to an apparatus used typically in genetic transformation of the higher plant. In particular, the present invention relates to a laser apparatus for boring a hole through a cell wall of a plant for injecting foreign genetic materials and a genetic recombination method using this apparatus.

In the conventional genetic transformation of the higher plant, typically, a premature embryo is taken out from a seed cut from a panicle of a mature plant and cultured or a seed with the seed coat thereof removed is budded. There is adopted a method of culturing an embryo or a porphyritic texture by using a means for accelerating and injecting inactive carrier particles coated with a replicative substance of a nucleic-acid organization into a somatic cell obtained by cutting out a split porphyritic texture from a nursery plant as disclosed in the specification of U.S. Pat. No. 5,149,655 with the title "Apparatus for Genetic Transportation." The method is referred to as the particle-mediated genetic-transformation method.

By the way, in the particle-mediated genetic-transformation method, since a somatic cell of a plant is protected by a cell wall with a thickness of several microns which cell wall is composed of mainly layers of a very stiff fiber material made of cellulose and pectin layers between the cellulose layers, in order to break the wall of the somatic cell, physical bombardment of tungsten or gold particles with a diameter of about 1.2 microns into the embryo is required. For this reason, a pistol or an air rifle is used.

When a particle-mediated genetic transformation is carried out by means of a pistol or an air rifle, however, it is feared that the somatic cell of the embryo itself is damaged by the energy of the particles used in the bombardment. Thus, the resulting yield is not necessarily high. As a result, it is necessary to prepare a large number of embryo cells and a large amount of replicative substance of the nucleic-acid organization. On the top of that, the use of a pistol or an air rifle is dangerous. In addition, it is also necessary to get a license of using explosives of firearms, giving rises a lot of miscellaneous related work.

OBJECT AND SUMMARY OF THE INVENTION

It is an object of the present invention to increase the yields of the embryo cells and the replicative of a nucleic-acid organization and to carry out the genetic recombination work at a high degree of efficiency by eliminating the danger of using a pistol or a rifle gun and the need for a license to use the pistol or the air rifle.

The present invention addresses the problems described above. It is thus an object of the present invention to provide a genetic recombination laser apparatus which at least comprises an optical system and means for positioning the focus of a converged light output by the optical system at an arbitrary location on a specimen which optical system comprises: a laser light source; pulse control means for carrying out pulse control on the laser light source at a high speed; conversion means for converting a laser light generated by the laser light source into a shortwave laser light; and a lens for converging the shortwave laser light output by the conversion means, wherein the energy of the laser light converged on the specimen is set at a level higher than the bonding energy of a material composing the cell wall of the specimen.

The laser light converged on the specimen is an extreme ultraviolet light which must have a wavelength of equal to or smaller than 300 nm.

The duration time of each pulse generated by the pulse control means must be set at such a value that, with the relation to a peak output of the light source taken into consideration, gives energy enough for the laser light to pass through the material composing the cell wall of the specimen.

A control means is provided for relating timing for positioning the focused light on the specimen to the timing with which pulses are generated by the pulse control means.

The laser light focused on the specimen is the fifth harmonic of a neodymium YAG (Nd:YAG) laser having a wavelength of 213 nm.

A means for positioning the focus of the fifth harmonic of a neodymium YAG (Nd:YAG) laser light having a wavelength of 213 nm on the specimen utilizes the second harmonic with a wavelength of 532 nm which is generated in the generation process of the fifth harmonic.

The genetic recombination laser apparatus is used for boring an infinitesimal hole on a specimen to undergo genetic transformation by applying a laser light to the cell wall of the specimen. The infinitesimal hole is used for injecting foreign genetic material into the somatic cell of the specimen. To be more specific, solution containing the foreign genetic material is injected through the infinitesimal hole in a so-called genetic recombination method which implements code manifestation of the foreign genetic material effectively. With this genetic recombination laser apparatus and the genetic recombination method, the problems described above can be solved.

In the configuration described above, the fifth harmonic with a wavelength of 213 nm of the neodymium YAG (Nd:YAG) laser light has a photon energy of 5.8 eV, a value greater than a C—C chemical bonding energy of 3.2 eV. In addition, a number of plants generally have an extremely high absorption factor with respect to the extreme ultraviolet light. Thus, when the photon energy of the fifth harmonic of the laser light exceeds a threshold value, the so-called ablation is generated. The abrasion can be used for boring an infinitesimal hole with ease through the stiff cell wall with a thickness of several microns. The cell wall is mainly cellulose $(C_6H_{10}O_5)_n$ protecting a premature embryo cell of the higher plant. In addition, it is possible to keep thermal injuries to the somatic cell and injuries caused by a shock wave resulting from an opto-acoustical effect at an extremely low level.

DESCRIPTION OF THE PREFERRED EMBODIMENTS

Figure 1:
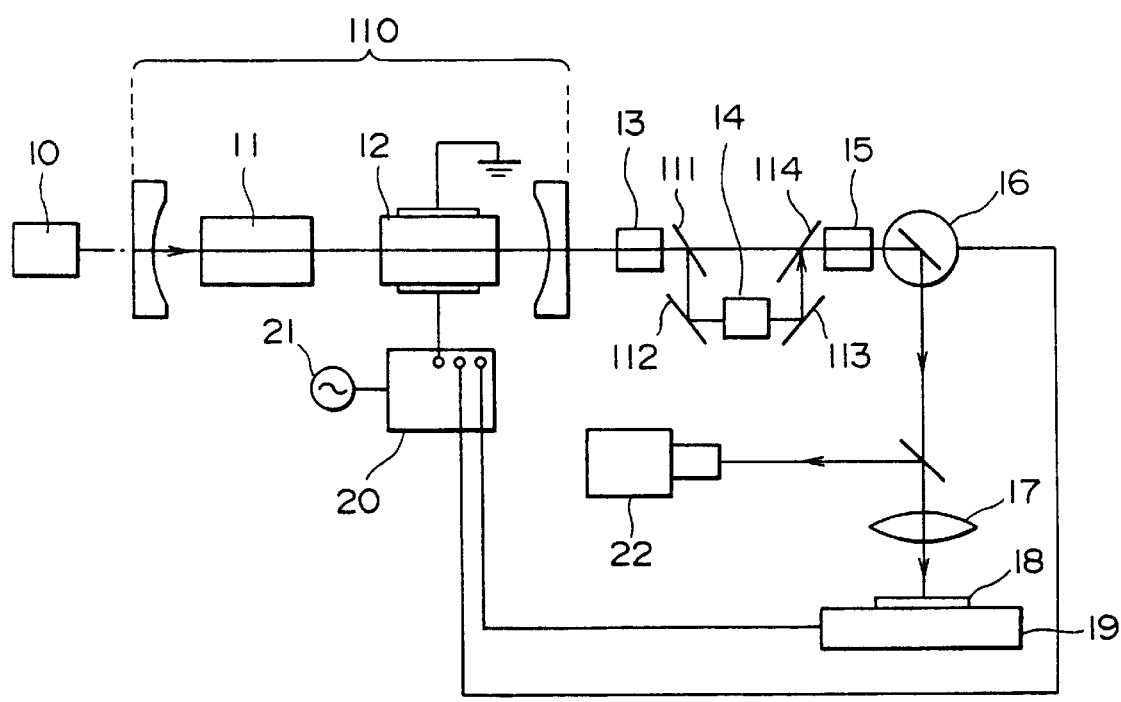
FIG. 1 is a diagram showing a genetic recombination laser apparatus provided by an embodiment of the present invention.
Figure 2:
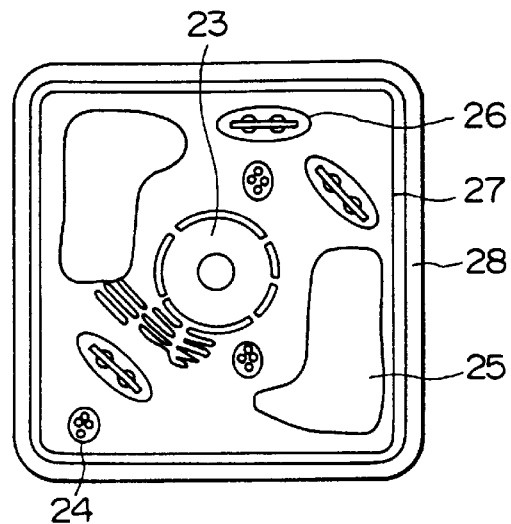
FIG. 2 is a diagram showing a model of a somatic cell of a plant specimen wherein a hole is bored through the cell wall thereof by means of the genetic recombination laser apparatus provided by the present invention.

The present invention will become more apparent from the following detailed description of a preferred embodiment with reference to FIGS. 1 to 3.

Figure 3A:
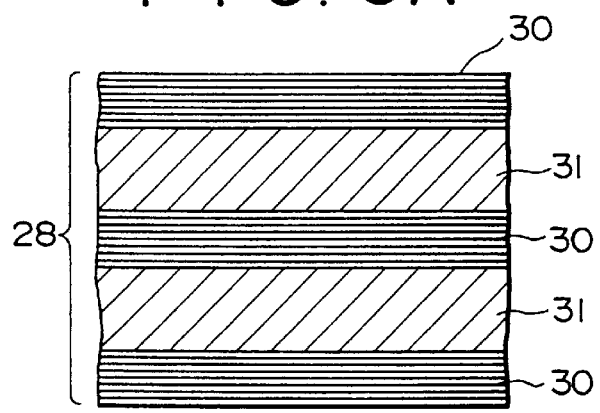
FIG. 3A is a diagram showing a cross section of the cell wall of the plant specimen through which a hole is to be bored by means of the genetic recombination laser apparatus provided by the present invention.
Figure 3B:
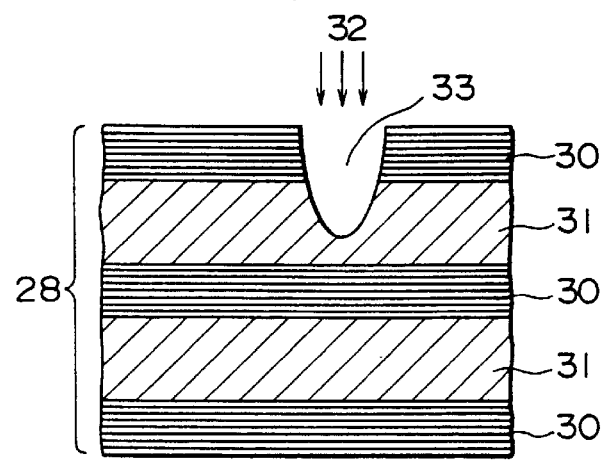
FIG. 3B is a diagram showing a process for boring the hole by ablation.

FIG. 1 is a diagram showing a genetic recombination laser apparatus provided by an embodiment of the present invention. FIG. 2 is a diagram showing a model of a somatic cell of a plant specimen wherein a hole is bored through the cell wall thereof by means of the genetic recombination laser apparatus provided by the present invention. FIG. 3A is a diagram showing the cross section of the cell wall of the plant specimen through which a hole is to be bored by means of the genetic recombination laser apparatus provided by the present invention. FIG. 3B is a diagram showing a process for boring the hole by ablation.

First of all, the configuration and the operation of the genetic recombination laser apparatus provided by the present invention are explained by referring to FIG. 1. Reference numeral 10 shown in the figure is a semiconductor laser light with a wavelength of 808 nm. The semiconductor laser light is used for exciting an Nd:YAG crystal denoted by reference numeral 11, a typical solid-state laser medium located in a resonator 110 having mirrors at both ends thereof. The excitation of the Nd:YAG crystal 10 causes an infrared light with a wavelength of 1,064 nm to oscillate. Reference numeral 12 is an acoustic optical device provided in the same resonator 110 as the Nd:YAG crystal 11. By varying the amount of loss incurred in the resonator 110, a narrow pulse light with a high peak output is generated.

A narrow pulse light having a high peak output described earlier is applied to a lithium triborate (LBO) 13, a first nonlinear optical crystal, as an incident light, causing a green light with a wavelength of 532 nm, a second harmonic, to be generated along with an infrared light with a wavelength of 1,064 nm. Then, the green light with a wavelength of 532 nm is reflected by mirrors 111 and 112 before being applied to a beta barium borate (β-BBO) 14, a second nonlinear optical crystal, as an incident light to generate an ultraviolet light with a wavelength of 266 nm. Then, an ultraviolet light with a wavelength of 213 nm is generated by a beta barium borate (β-BBO) 15, a third nonlinear optical crystal. It should be noted that the 213-nm wavelength is a reciprocal number of a sum frequency of the frequency of the ultraviolet light generated by the β-BBO 14 and reflected by a mirror 113 and the frequency of the infrared light generated by the LBO 13 and passing through the mirror 111 and a mirror 114. The ultraviolet light with a wavelength of 213 nm is used as a light applied to the specimen. In addition to the ultraviolet light with a wavelength of 213 nm, the β-BBO 15 also generates a green light with a wavelength of 532 nm.

The ultraviolet light with a wavelength of 213 nm radiated by the β-BBO 15 is reflected by a galvano mirror 16 serving as a polarization device and passes through a lens 17 before being converged on a specimen 18. The specimen 18 is placed on a stage 19, the position of which can be adjusted. The movement of the stage 19 is controlled by a controller 20 that is connected to a signal source 21. At the same time, the controller 20 also controls the acoustic optical device 12. Thus, it is possible to synchronize the laser light pulses with the position of the specimen 18. A television camera 22 is used for monitoring the positioning state of a laser light spot focused on the specimen 19 and for detecting the green light with a wavelength of 532 nm radiated by the β-BBO 15 and reflected by the specimen 18.

It should be noted that, instead of positioning the specimen 18 by controlling the stage 19, the position of the focused laser light on the specimen 18 can be of course shifted by using an optical means, a mechanical means or a means combining the optical and mechanical means. It is worth noting that these alternative means are not shown in the figure.

FIG. 2 is a diagram showing a model of a somatic cell of a plant specimen wherein a hole is bored through the cell wall thereof by means of the genetic recombination laser apparatus provided by the present invention. As a plant cell, typically, a cell of a premature embryo or split porphyritic texture of the higher plant to undergo genetic transformation is used. The plant cell comprises a nucleus 23, mitochondria 24, vacuoles 25, a chlorophyll 26, a cell membrane 27 and a cell wall 28.

FIG. 3A is a diagram showing the cross section of the cell wall 28 of the plant specimen through which a hole 33 is to be bored by means of the genetic recombination laser apparatus provided by the present invention and FIG. 3B is a diagram showing a process for opening the hole by ablation. As shown in the figure, the cell wall 28 comprises cellulose fiber layers 30 and pectin substance layers 31 stacked on each other alternately. A hole 33 is bored through the cell wall 28 by a laser light 32 with a wavelength of 213 nm generated by the genetic recombination laser apparatus. As is also obvious from the figure, the cell wall 28 is formed firmly by some layers of cellulose fiber 30 and pectin substance 31, enclosing the interior elements of a somatic cell.

As described above, in a conventional particle-mediated genetic transformation, it is necessary to physically break the cell wall 28 including the cell membrane 27 by bombardment of tungsten or gold particles with a diameter of about 1.2 microns. On the other hand, according to the present invention, the hole 33 is bored through the cell wall 28 by applying an extreme ultraviolet laser light to the cell wall 28 as shown in FIG. 3B. Then, solution containing foreign genetic material is injected through the hole 33 in order to perform code manifestation of the foreign genetic material effectively.

The photon energy of the extreme ultraviolet light with a wavelength of 213 nm used in the present invention is given as follows:

$$\text{Photon energy} = 1.24/\text{light wavelength (microns)}$$
$$= 1.24/0.213$$
$$= 5.8 \text{ (eV)}$$

The photon energy has a value sufficiently greater than 3.2 eV, the chemical bonding energy of the basic structure of an organic substance C—C.

In addition, the laser light with a wavelength of 213 nm developed by inventors of the present invention has an average output of 400 mW, a pulse width of 50 nsec and a repetition frequency of 7 KHz. By the way, the following equation holds true:

Average output (W)=peak output (W)×pulse width (sec)×repetition frequency (Hz)

Accordingly, it is obvious that a high peak output of greater than 1 KW is obtained. It is also obvious from these pieces of data that the extreme ultraviolet light with a wavelength of 213 nm can be used as a preferred light to be generated by the light source employed in the genetic recombination laser apparatus.

In addition, since the present laser light has a short wavelength, has no aberration and has good coherency, the light can be converged to a spot size (=wavelength/the number of apertures) which is limited only by diffraction even if a lens with a low number of apertures (an NA of about 0.2) is used. That is to say, even with a lens with an NA of 0.2, the laser light can be converged to a spot of about 1 micron with ease. In this case, the fluence is given as follows:

$$\begin{aligned}\text{Fluence} &= \text{average output (W)} \times \text{pulse width (sec)} / \\ &\quad \text{illumination area (cm}^2\text{)} \\ &= 400 \text{ (mW)} \times 50 \text{ nsec} / (\pi \times 0.5^2)(\mu m^2) \\ &= 2.54 \text{ (J/cm}^2\text{)}\end{aligned}$$

In addition, at a wavelength of 213 nm, the absorption of light by the cell wall 28 is extremely good. As a result, the hole 33 can be bored through the cell wall 28 in a short period of time by ablation. On the top of that, by using a light with a wavelength of about 200 nm, only few DNA injuries will be resulted in in the interior of the somatic cell of the plant.

Let us compare the value 2.54 (J/cm$^2$) of the fluence found above with, for example, an ArF excimer laser light having a wavelength of 193 nm used in the straightening of a cornea with an abnormal refraction power. Since the ablation speed is 0.5 microns/pulse at a fluence of 50 to 250 mJ/cm$^2$, about the same ablation speed as that of the ArF excimer laser light can be obtained for a cell wall 28 with a thickness of several microns if a fluence of 2.54 J/cm$^2$ exists at a wavelength of 213 nm. As a result, it is possible to bore a hole with a diameter of about 1 micron with one to several pulses through the cell wall 28.

What is claimed is:

1. A genetic recombination laser apparatus comprising:

a controller connected to a signal source;

an optical system having at least a laser light source comprising an Nd:YAG laser excited by a laser light generated by a semiconductor laser for generating laser light, pulse control means connected to said controller for carrying out pulse control on said laser light source, means for reducing the wavelength of said laser light generated by said laser light source to a first component having a wavelength of about 530 nm and a second component having a wavelength of about 213 nm and a lens for converging said laser light comprising said first component and said second component to a spot of about 1 $\mu$m; and means for positioning the focus of said laser light converged by said lens at any arbitrary location on a specimen including a movable stage under control of the controller on which the specimen is placed and a television camera for monitoring the position of the focus of the laser light converged by the lens on the specimen, wherein said second component of said laser light converged on said specimen is set at a fluence of about 2.54 J/cm$^2$ and is effective in one to several pulses to bore a hole of 1 $\mu$m diameter through a cell wall of a somatic cell of said specimen.

2. A genetic recombination laser apparatus according to claim 1 wherein said pulse control means sets the duration of each pulse generated thereby at a time length during which said laser light converged on said specimen can pass through said cell wall.

3. A genetic recombination laser apparatus according to claim 1 further comprising a means for synchronizing pulse generation timing of said pulse control means with timing for positioning said laser light generated by said optical system on said specimen.

* * * * *